United States Patent [19]

Cocchi

[11] 4,439,303

[45] Mar. 27, 1984

[54] CRYSTALLOGRAPHICALLY-ORIENTED SPATIALLY-DISPERSED CONDUCTIVE FIBER ELECTRODE

[76] Inventor: Maurice Cocchi, 4007 W. 27th Ave., Denver, Colo. 80212

[21] Appl. No.: 393,128

[22] Filed: Jun. 28, 1982

[51] Int. Cl.³ .................... G01N 27/26; B01K 3/04
[52] U.S. Cl. .................................. 204/434; 204/294
[58] Field of Search ................... 204/294, 434, 1 T

[56] References Cited

U.S. PATENT DOCUMENTS

| | | | |
|---|---|---|---|
| 3,634,569 | 1/1972 | Emanuelson et al. | 264/105 |
| 3,708,451 | 1/1973 | McWhorter et al. | 260/29.8 |
| 3,726,638 | 4/1973 | Gellon et al. | 156/276 |
| 3,853,610 | 12/1974 | Byrne | 117/161 |
| 3,855,099 | 12/1974 | Matson | 204/294 |
| 3,856,574 | 12/1974 | Amagi et al. | 136/120 |
| 4,094,897 | 6/1978 | Nagasawa et al. | 264/105 |
| 4,108,754 | 8/1978 | Fleet et al. | 204/263 |
| 4,118,532 | 10/1978 | Homsy | 428/294 |
| 4,127,634 | 11/1978 | Joo | 264/105 |
| 4,197,180 | 4/1980 | Woodward | 204/275 |
| 4,236,993 | 12/1980 | Muller et al. | 204/294 |
| 4,265,727 | 5/1981 | Beckley | 204/242 |

Primary Examiner—John F. Niebling
Attorney, Agent, or Firm—Crandell & Polumbus

[57] ABSTRACT

An electrode for use in electrochemical reactions such as electrochemical stripping analysis comprises a plurality of generally parallelly oriented and laterally spatially displaced electrically conductive fibers which are separated and held in a core by electrically insulating bonding material which substantially completely fills the lateral spaces between the fibers. The fibers, preferably carbon fibers, have a crystallographic structure of a plurality of maximum electrical conducting planes extending generally parallel to the fiber. The bonding material is substantially electrically insulating and may be a polyester or epoxy resin. The electrode is formed by saturating a plurality of fibers with fluid resin bonding material, compressing the resin saturated fibers by passing them through a form, allowing the bonding material to harden and forming an electrode face on the resulting core which extends transversely with respect to the fibers to maximumly expose the conductivity planes of the fibers at the electrode face.

12 Claims, 11 Drawing Figures

CRYSTALLOGRAPHICALLY-ORIENTED SPATIALLY-DISPERSED CONDUCTIVE FIBER ELECTRODE

This patent is subject to the reservation to the government of the United States of America of a non-exclusive, irrevocable, royalty-free license with power to grant sublicenses for all governmental purposes.

This invention relates to an electrode for creating electrochemical reactions and is particularly useful for electroanalytical chemistry and even more specifically for electrochemical stripping analysis.

Electrochemical stripping analysis, sometimes known as stripping voltammetry or simply voltammetry, refers to an electrochemical analytical technique for determining the existence and quantity of selected types of chemical elements, even in trace amounts. Electrochemical stripping analysis is currently widely used in determining the quantities and types of chemicals constituting air and water pollution and for making certain types of organic or biological determinations, among other uses.

In electrochemical stripping analysis, the electroactive species to be determined is concentrated electrolytically at, or plated out on, a measuring electrode, usually by maintaining the electrode at a predetermined electrical potential. Thereafter the concentrated or plated out electroactive species is transferred back into the solution, i.e., stripped off, by the reverse electrolytic process of changing the voltage at the electrode with respect to time to a reverse potential. The voltage and current are monitored during reverse electrolysis. When the potential reaches a predetermined magnitude characteristic of the electroactive species plated out, a current commences flowing indicating that the electroactive species is stripping off of the electrode and going back into solution. A graph of the voltage and current characteristics is derived and analyzed. The voltage at which the current peak occurs when the plated material is stripped off and transferred into solution is characteristic of the electroactive species in the solution which was initially plated out. The area of the peak is proportional to the concentration of the electroactive species in the solution.

Successful electrochemical stripping analysis requires achieving sufficient sensitivity, i.e., a good high signal to noise ratio for determining the size of the current peak, and sufficient selectivity, i.e., good sharpness or narrowness of the peak to relate its occurrence to a stripping voltage characteristic of the electroactive species, possibly in solutions containing concentrations of other types of substances at substantially higher concentrations. Sensitivity is decreased by increased background current flowing during the stripping process. The background current comprises primarily a capacitive current involved in charging the two layers or atoms in the solution adjacent the active electrode face to a potential opposite of that at the electrode face. Other contributions to background current result from impurities in the solution. Selectivity relates primarily to the efficiency by which the plated electroactive species is concentrated at, plated on and stripped off of the electrode face. In stripping analysis, sensitivity is largely dependent on a uniformity in electrochemical bonding of the electroactive species to the electrode face. If the bonds are built up with uniform energy content, they will likewise be broken during stripping at a more sharp, uniform voltage.

The surface area of the electrode face, the potential distribution over the surface of the electrode face, and the porosity of the electrode face, among other factors, significantly influence the amount of material plated onto and stripped off of the electrode face. The area of the electrode face, of course, defines the area upon which the electroactive species can be plated out, provided equal potential exists over the electrode surface. Unequal potential distribution over the electrode face results in areas of decreased electrolytic activity, which results in plating at nonuniform energies. Uniform plating out is presumed when calculating the concentration of electroactive species. The porosity of the electrode surface can retain or trap atoms of the plated out electroactive species during stripping. The current peak will not accurately reflect the amount of electroactive species plated onto the electrode, since limited amounts remain after stripping.

Many other factors influencing electrochemical stripping analysis are also known and appreciated. Many of these same factors are also considerations in achieving highly efficient and effective electrochemical reactions from electrodes used in a variety of different types of electrochemical applications, other than electrochemical stripping analysis.

SUMMARY

According to its broad aspects, the present invention pertains to an electrode comprising a plurality of generally parallel and relatively fine elongated conductive fibers of crystallographically-oriented material, such as carbon fibers, wherein the crystallographic planes present maximum conductivity paths along the length of each of the fibers. An insulating bonding material, such as a resin, is bound to and insulates and separates each of the fibers and retains the plurality of fibers in an electrode core structure. The electrode face is formed transversely with respect to the parallel extending fibers to maximumly expose the conducting planes to electron flow. An insulating jacket surrounds the core to electrically insulate the core except at the electrode face. An electrical connection is made to each of the fibers at their ends opposite of the electrode face, preferably by plating a single metallic electrode to the core at the opposite end of the electrode face.

According to another aspect of the invention which pertains to fabricating the electrode, the plurality of fibers is impregnated with an insulating bonding material and then the fibers are preferably drawn into a form or mold to compress the bonding material and flow it around and along the fibers, driving out the entrained gasses, and encompassing any minute voids or spaces not filled by the bonding material during impregnation. Thereafter, the bonding material is allowed to harden. The electrode face is formed by cutting through the core of material transversely with respect to the fibers and polishing the resulting surface. The shape of the core material can be machined to desired shapes or left in the original form created. The ratio of the fibers to the volume of bonding material can be controlled by the degree of compression and the viscosity of the bonding material.

A multiplicity of distributed, active sites for electrolysis are created at the electrode face. Each active site is defined by the end of a fiber, and each of the fibers is separated from its neighbor by insulating bonding material. By orienting the crystallographic planes of each parallel fiber to provide the greatest conductivity along the length of the fibers, each active site at each fiber end is more uniform or similar in potential compared to all of the other active sites. A uniform potential distribution exists over the whole electrode face. This is a distinct advantage over certain prior art glassy carbon electrodes, for example, where the crystallographic planes are randomly distributed and the active sites are of randomly different potentials. Each of the active sites is more uniformly effective in concentrating and plating out the electroactive species and in stripping off the electroactive species during reverse electrolysis because of favorable spatial relationships enhancing diffusion and uniform voltage potential fields at each fiber end. The whole surface area of the electrode is more efficiently utilized because of the independent behavior of each fiber end. A bonding material such as resin has very low surface porosity. Stripping of the plated out species occurs more completely over a narrow range of voltages without significant residual electroactive species remaining at the electrode face. Residual capacitive or background current is significantly reduced because the bonding material is nonconductive and the substantial majority of current flow is transferred from the fiber ends at the active sites, thereby contributing to electrolysis. In contrast, the random distribution of conductivity planes in glassy carbon and the resulting sites of nonuniform potential distribution, allow capacitive or background current to be introduced into solution because of the ineffective or reduced plating which occurs at the reduced-activity sites. In its preferred form, when constructed of carbon fibers and resin, the electrode of the present invention can be fabricated quickly at a relatively low cost.

Other advantages, improvements and features of the electrode of the present invention can be better understood by reference to the following detailed description of preferred embodiments, and from the drawings.

DRAWINGS

Figure 5:
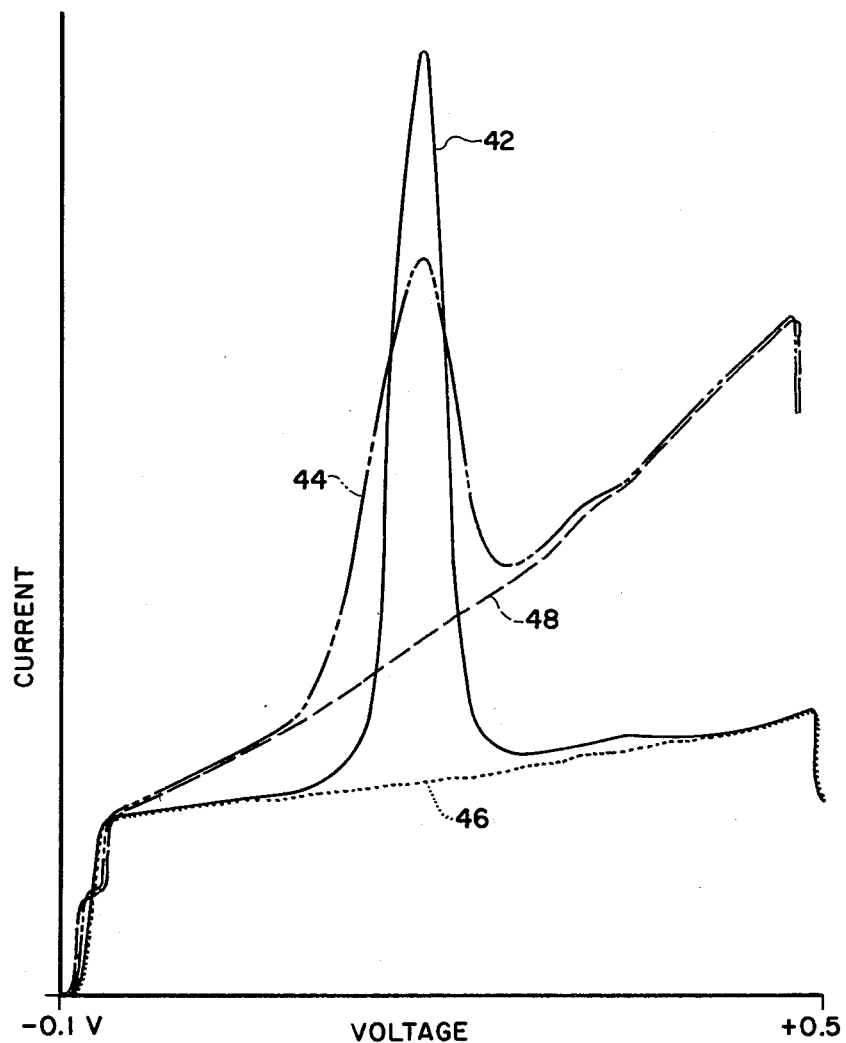

FIG. 5 is a voltagram substantially to scale illustrating the performance of the electrode of the present invention in comparison to a glassy carbon electrode. The voltagram of the electrode of the present invention is shown by a solid line and its base line is shown by a line of short dashes. The voltagram of the glassy carbon electrode performance is illustrated by a line broken by consecutive pairs of dashes, and its base line is shown by a line of long dashes.

FIGS. 6, 7, 8 and 9 are sequential illustrative representations of steps involved in a method of fabricating the electrode of the present invention.

Figure 10:
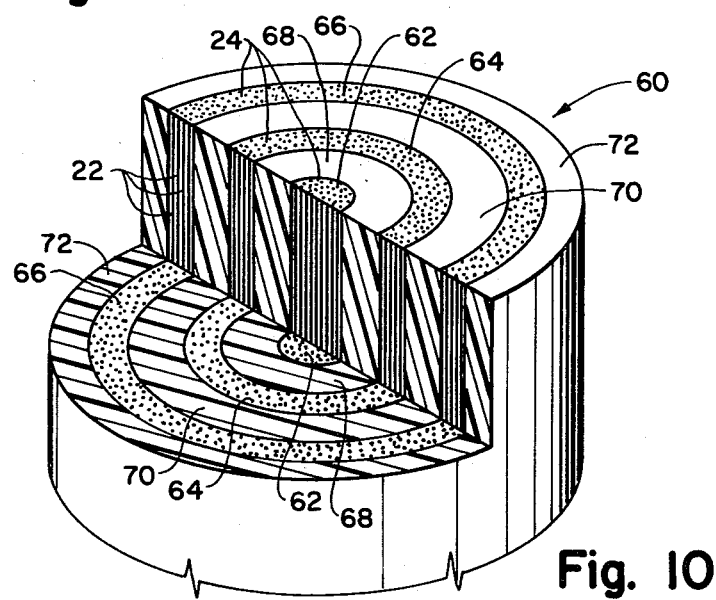
Figure 6:
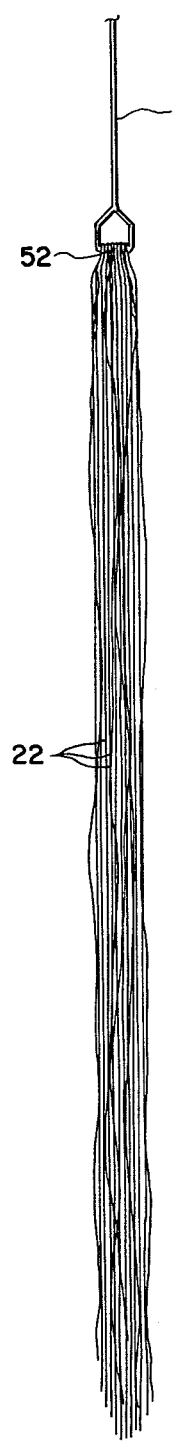

FIG. 10 is a perspective view of another embodiment of the present invention which incorporates multiple concentric electrode cores and insulating rings, with a portion sectioned out at the electrode face to better illustrate the concentric electrode cores and insulating rings.

PREFERRED EMBODIMENT

Figure 1:
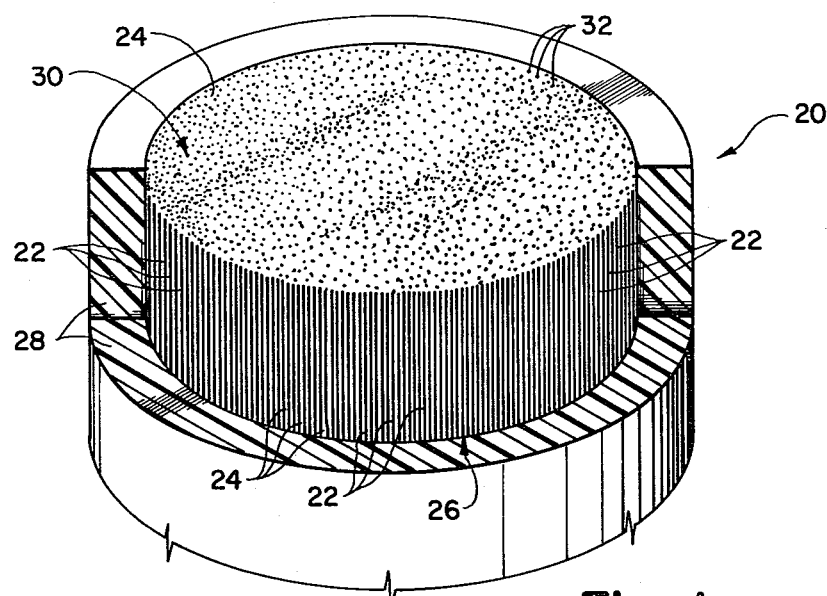
FIG. 1 is a partial perspective view of the electrode of the present invention, with a portion of the outer insulation cut away to illustrate the core and the electrode face.
Figure 2:
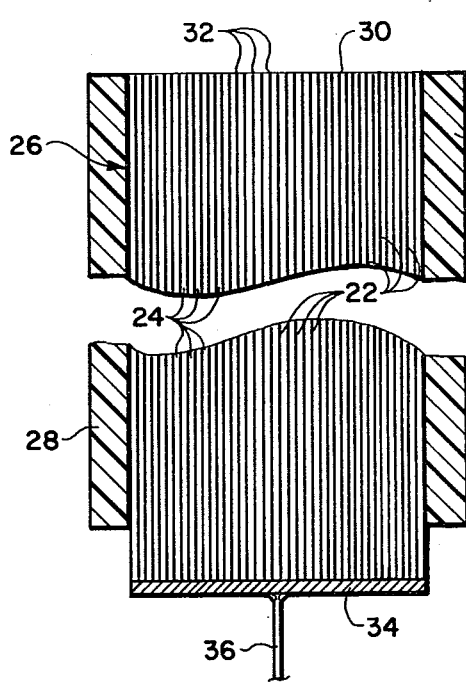
FIG. 2 is a vertical section view through the electrode with a longitudinal center portion broken out.

One embodiment 20 of the electrode of the present invention is illustrated in FIGS. 1 and 2 as comprising a plurality of generally parallelly oriented conductive fibers 22 which are laterally spatially separated by insulating bonding material 24 from one another. The fibers 22 and hardened bonding material 24 define an electrode core 26 to which a layer or jacket of insulation 28 is attached or bonded around the lateral exterior. An electrode face 30 is formed transversely across the electrode 20. The electrode face 30 preferably intersects each of the fibers 22 generally perpendicular to the elongated length of the fiber 22. At the point of intersection of each fiber 22 with the face 30, an active site 32 (FIG. 4) for electrolysis occurs. The electrode face 30 is polished to a high smoothness or resolution. The bonding material 24 preferably is of extremely low porosity and, when polished, the bonding material 24 at the face 30 presents a very low or minimal porosity.

At the end of the electrode core 26 opposite the electrode face 30 a metallic conductor 34 is plated as a layer onto the core 26. The metallic conductor 34 directly electrically connects to the ends of the fibers 22 opposite those defining the active sites 32 (FIG. 2). In lieu of the conductor 34, conducting cements or a liquid mercury drop covering the end of the electrode core could be employed. An electrical conductor such as that at 36 is electrically connected to the metal plate 34 for the purpose of directly conducting current to and from each of the fibers 22.

Figures 3A, 3B:
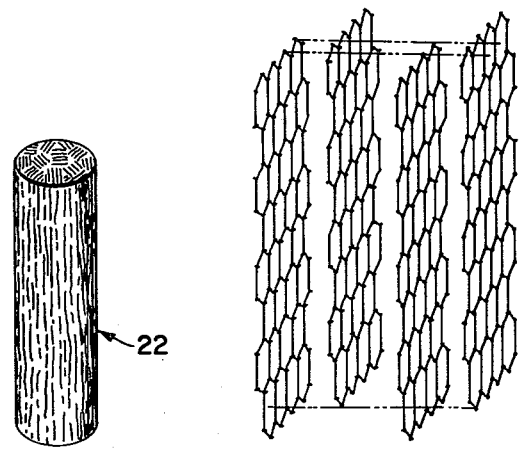
FIG. 3A is a perspective view of a segment of a single carbon fiber of the electrode, illustrating the parallel conductivity planes.
FIG. 3B is a schematic view of the crystallographic planes giving rise to parallel conductivity planes in carbon fibers.

The fibers 22 are preferably carbon or graphite. As shown in FIG. 3A, each fiber 22 has planes of greatest conductivity extending parallel along the length of each of the fibers as compared to planes of diminished conductivity and increased resistance extending laterally of the fibers 22. As shown in FIG. 3B, each conductivity plane is defined by a regular crystallographic structure along which the electrons will readily travel. Since each parallel crystallographic structure is not atomically connected, substantially diminished conductivity for electrons exists laterally between the parallel crystallographic planes.

By arranging the planes of greatest conductivity to extend along the length of each of the fibers, the electrical potential at each of the active sites 32 (FIGS. 2 and 4) will be more uniformly equal, thereby establishing a more uniform distribution of equal potential over the whole face 30 of the electrode. A significant improvement over prior art glassy carbon type electrodes results because in such prior art electrodes, the planes of greatest conductivity are randomly oriented, thereby establishing active sites of unequal potential distribution on the face of the glassy carbon electrodes. In the present invention, the relatively equal potential at each of the active sites is very important in achieving good electron transfer and diffusion at the electrode face.

Although a carbon or graphite fiber 22 is preferred, other fiber material having relatively high purity, conductivity, tensile strength, and a crystallographic structure with the planes of greatest conductivity generally parallel to the longitudinal extent of the fiber, and with relatively uniform diameter and roundness, is contemplated within the invention. A relatively high purity assures substantially uniform conductivity and hence potential distribution at the electrode face. High tensile strength is an important characteristic in certain fabrication techniques, as is described subsequently. A relatively uniform diameter and roundness tends to achieve a more uniform density or spatial relationship between neighboring fibers and the bonding material 24. One type of carbon fiber which has proved acceptable in the present invention is Union Carbide "Thornel" 50 (PAN) Carbon Fiber Grade WYR 15 1/0.

The bonding material 24 is chosen to accommodate the chemical characteristics of the electrode working environment. In addition, the bonding material 24 should be capable of rigidly setting and retaining the fibers 22. The bonding material 24 should also present a very minimal porosity and should be capable of being polished or finished to a smooth surface at the electrode face 30. Of course, the bonding material 24 should possess electrically insulating characteristics so as to separate each of the conductive fibers 24 from one another and to confine the electrolytic activity to the active sites 32. The bonding material should be hard or capable of being made hard during polishing to avoid being drawn over the ends of the fibers 22 during polishing to insulate the active sites 32. The bonding material should also be relatively free of impurities to enhance its electrical insulating characteristics. Catalytic setting resins, such as epoxy and polyester, and thermosetting phenolic type resins appear the most desirable. A Plasticrafts Impact polyester resin has been successfully employed in the invention.

The insulation jacket 28 is formed around the core 30. The purpose of the insulation jacket 28 is to confine the electrolysis to the electrode face 32 and prevent electrolytic activity on the lateral sides of the core 26. The insulating jacket 28 can be formed by a coating or layer of bonding material.

The typical electrical resistivity of the preferred type of carbon fibers is approximately 0.00095 ohm-cm. The electrical resistivity of the preferred hardened insulating material is greater than in the realm of 5,000,000 ohm-cm. It can be seen, therefore, that the electrical conductivity and resistance characteristics of the carbon fibers and the bonding material in a preferred embodiment differ from one another by in the realm of nine magnitudes (1,000,000,000).

Figure 4:
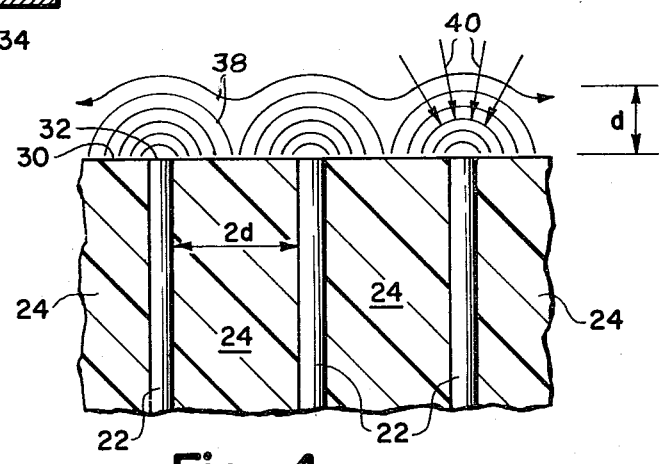
FIG. 4 is an enlarged view of a portion of FIG. 2 at the electrode face, illustrating voltage potential gradients and diffusion paths of ions adjacent the electrode face toward the active sites at the ends of the fibers.

The fiber density is determined by the spatial relationship between the fibers 22 and is defined by the distance by which adjacent or neighboring fibers 22 are separated by the bonding material 24, as shown in FIG. 4. A typical fiber density is approximately thirteen million fibers, each of which is approximately six micrometers in diameter, per square inch of electrode face. The fiber density can be varied in accordance with optimum conditions for the particular application. In electrochemical stripping analysis electrodes, there are certain important considerations regarding the fiber density. In situations where there is relative motion between the electrode and the solution, as with a rotating electrochemical stripping electrode, a shear plane is established in the liquid at a distance d from the face 30 of the electrode, as shown in FIG. 4. At high electrode rotational speeds, the concentration of the electroactive species is always approximately constant along the outside of the shear plane, due to the relative motion. Diffusion of the electroactive species only occurs across the distance d, as shown in FIG. 4. Under such circumstances, the spacing between the edges of the fibers 22 need not be any greater than 2d in order to limit the constraints of diffusion to a minimum. In general, distance d will be at least equal to or greater than the normal distance between two electroactive species in solution, or a two atom spatial separation. The distance d is a function of the relative affinity of the fluid molecules for themselves in the solution as compared to their affinity for the electrode face 30. The optimum spacing distance (2d) between adjoining fibers 22 appears to be inversely related to the degree of aversion between the electrode face and the fluid. For example, a more hydrophobic electrode face will result in a shorter distance 2d in the case of a water based solution. Polyester bonding material is relatively hydrophobic, while the ends of the fibers 22 are relatively more hydrophilic.

Improved enhancement of favorable diffusion characteristics is understood from FIG. 4. Each of the fiber ends at the active sites 32 presents its own electrostatic field potential which does not significantly nteract with the field potential of a neighboring fiber at its active site. The concentric field potential gradients 38 cause diffusion of the electroactive species perpendicular thereto along the arrows 40 and concentrate those ions at the active sites 32. Each fiber end behaves more as a truly independent active site. The voltage potential strength between the active site 32 and the solution concentration plane at distance d is greater, and the voltage potential gradients are relatively independent of the neighboring active sites 32. Diffusion flow to each of the active sites is relatively independent of diffusion flow to neighboring active sites, and a greater transport of the electroactive species to and from the active sites results. Since each active site 32 is more independent, the bonding energy of the electroactive species is more uniform during plating out and stripping off. This presents a significant improvement in diffusion flow over a relatively large totally conducting surface, such as that of prior art electrodes. The electrostatic potential gradients or concentration in the center of large totally conducting electrodes is random and results in less electron diffusion and in more nonuniformity in bonding energy. Accordingly, the quantity of electroactive species plated out on the center of such a prior art electrode is reduced and the plating which does occur occurs and at more fluctuating voltages. In contrast, the present invention achieves nearly a uniform plating out of the electroactive species at each of the active sites 32 over the whole electrode face 30.

The increased diffusion available from the present invention is related to an increase in efficiency in plating out the electroactive species and in stripping off the electroactive species during reverse electrolysis, due to the spatial distribution of the fiber ends and independent behavior of the electroactive species at each active site. By causing the electroactive species to plate out at a more uniform bonding voltage, the electroactive species strips off at a more uniform voltage. The resulting voltagram is more easily analyzed to determine the type of electroactive species plated out and its concentration.

Some of the advantages of the present invention are illustrated by FIG. 5. Curve 42 in FIG. 5 is an actual voltagram derived by use of an electrode 20 of the present invention. Curve 44 in FIG. 5 is an actual voltagram derived by using a typical commercially available glassy carbon electrode. Both curves 42 and 44 are to the same scale. An electrode from which curve 42 was derived had the characteristics previously identified herein as preferred. The electrode face was 0.275 inches in diameter. Six hundred thirty thousand carbon fibers were present in the core. In the particular electrochemical procedure involved, both the electrode of the present invention and the glassy carbon electrode first had a gold film plated on the electrode face. Thereafter, arsenic was plated onto the gold film. Finally, the arsenic was electrolytically stripped off. What is significant in this procedure is that the differences in electrode faces are translated into the gold film plated out, although this is not visual microscopically, and the behavior in the gold film plated is visibly manifested by the stripping of the arsenic. In both cases, the gold film was plated from a 1.0 normal solution of HCl containing two milligrams of gold per twenty milliliters of solution. Plating proceeded without agitation. Similarly in both cases, arsenic was plated onto the gold film from a solution of fifty parts per billion arsenic in a 7.0 normal solution of HCl. Deposition of the arsenic proceeded for one hundred seconds at an electrode voltage of $-0.1$ volts with respect to a standard silver/silver chloride reference electrode. An equilibrium was allowed to occur for fifteen seconds at $-0.1$ volts. During deposition of the arsenic, both electrodes were rotated at thirty-six hundred r.p.m. During stripping, both electrodes were stationary. The resulting voltagrams 42 and 44 were derived during stripping.

The curve 42 is much more symmetrical about a vertical line through its peak. The narrowness of the peak of curve 42 allows it to be more precisely related to the particular stripping voltage characteristic of the particular type of electroactive type of species plated out, in this case arsenic. Greater selectivity in identifying the trace amounts of the electroactive species is achieved because the uniformity in bonding energy causes the sharper peak. As compared to the less symmetrical broader and wide peak of curve 44 caused by relatively more nonuniformity in bonding energy, it can be seen that the peak of curve 44 is more susceptible to error in selectivity of the plated out species.

Curves 42 and 44 also readily illustrate the significantly reduced amount of background current flowing into the solution from the electrode of the present invention as compared to the glassy carbon electrode. The slope of base line 46 for curve 42 and base line 48 for curve 44 are generally indicative of the amount of background current. It is apparent that for an given voltage along the horizontal axis in FIG. 5, a significantly greater background current flows from the glassy carbon electrode. The background current is basically useless in determining the amount of electroactive species plated out. Increased background current makes the calculation of the area under the peak of the curve more difficult and can decrease the amount of sensitivity. The relatively flat background current base line 46 of curve 42, combined with the symmetrical peak, allow more accurate calculations of the concentration of the electroactive species. Stated in an alternative manner, for approximately the same amount of plating out of electroactive species on the electrode of the present invention and on a glassy carbon electrode, a significantly lower amount of background current occurs with the present electrode. The significantly lower amount of background current reduces the amount of error in the calculations. Stated in another alternative manner, for the same amount of background current, a substantially greater amount of plating out of the electroactive species will occur with the present electrode. Both effects increase the efficiency of the present electrode.

The present electrode also behaves more predictably and reliably and with less variance than prior art glassy fiber electrodes. In a series of experiments similar to those used in deriving FIG. 5, the quantity of plated out electroactive species was determined under different conditions using both the electrode of the present invention and the glassy carbon electrode. The calculated concentrations derived from the voltagrams were compared to a known concentration placed in solution prior to the tests. The differences between the calculated concentrations obtained by electrochemical stripping analysis with the present electrode in one case and the glassy carbon electrode in the other case were compared to the known concentrations. A correlation coefficient was derived by linear regression. The correlation coefficient of the electrode of the present invention was 0.9987, while the correlation coefficient obtained from glassy carbon electrode was 0.9887. The difference in correlation coefficients can be translated into the degree of error which may be introduced in electrochemical stripping analysis simply because of the electrode. By using the electrode of the present invention, the measured concentrations, and hence the sensitivity, more accurately reflect the true concentration of the electroactive species in the solution.

The current conductivity of the present electrode also appears to substantially improved over the current conductivity of a glassy carbon electrode. Thus, not only are diffusion attraction characteristics enhanced, but the conductivity characteristics are also substantially improved. In the two electrodes used for comparison in the previously described experiments, the gross conductive area of the fiber ends at the electrode of the present invention was 0.0324 square inches. The gross conductive area of the glassy carbon electrode face was 0.0423 square inches. It was noted that the typical deposition currents from plating out gold on these electrodes, when held stationary, were thirty microamps with the present electrode and twenty microamps with the glassy carbon electrode. Thus, even though the gross conductive area of the electrode of the present invention was less than that of the glassy carbon conductive area, an increased current flowed from the electrode of the present invention. This increase in current can be related to plating efficiency by dividing the current by the effective conductive area. Such comparison shows that the electrode of the present invention has the capability of approximately twice the plating efficiency as a glassy carbon electrode. The electrode of the present invention appears, therefore, to be fundamentally better performing by achieving a better attraction diffusion of the electroactive species in solution, conducting more current, minimizing the background current, increasing diffusion characteristics and causing more uniform electroactive species bonding, among numerous other advantages.

The method of fabricating the electrode 20 is illustrated in FIGS. 6, 7, 8 and 9. Initially, a plurality of the carbon fibers 22 are accumulated in a bundle, and the fibers in the bundle are circumjacently clamped a short distance from one end of the bundle. The short extent of loose fibers extending between the clamped location and the ends form a loose head. The loose head is saturated in fluid resin bonding material and the resin is worked into all of the fibers. The resin-impregnated fibers at the loose end are compressed or compacted together to a diameter or cross section which is smaller than the final diameter or cross section of the final electrode core. The resin is allowed to dry and binds the fibers into a rigid head 52. A hole is drilled transversely completely through the rigid head 52 and a draw wire 50 is inserted through the head 52.

Figure 7:
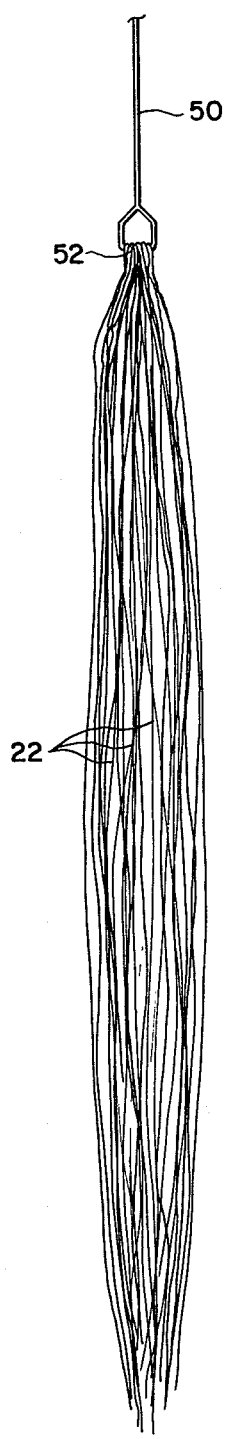

After the draw wire has been attached to the head 52, the remaining longer fibers are saturated or impregnated with unhardened fluid resin bonding material, as shown in FIG. 7. The resulting bundle is expanded by the resin adhesion along the length of the fibers. Conventional means for saturating the fibers can be employed, such as by dipping the fibers into a pool of the resin or flowing the resin onto the fibers.

Figure 8:
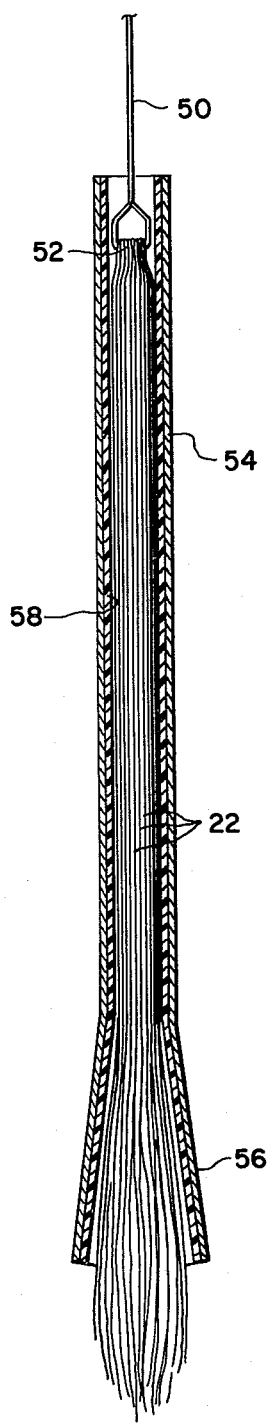

Next, the bundle of fibers which have been impregnated with resin are drawn through a form or mold such as a conduit 54, as shown in FIG. 8. The conduit 54 has a flared end 56 and an interior nonstick wall 58 formed of material such as Teflon. As the bundle is drawn into the tubular form 54, the bundle is compressed during movement through the flared end 56. The compression causes the viscous resin to flow along each of the fibers and fill any voids or areas not initially contacted by resin during the resin saturation step. A generally uniform spacing and density of fibers and resin material results. Movement of the bundle through the uniform diameter segment of the conduit 54 establishes and maintains an exterior configuration defined by the cross sectional open area of the form. Typically, the exterior configuration will be cylindrical because an annular conduit 54 will be employed. The resin is allowed to harden without disturbing the exterior formed configuration, thus rigidly structuring the fibers and resin bonding material in the shape created by drawing the bundle through the form.

Figure 9:
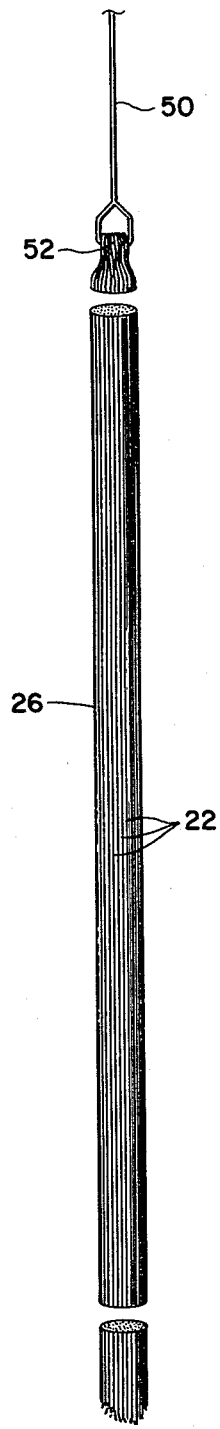

The resulting configuration of the fibers and hardened bonding material can be used directly. Alternatively, the hardened configuration can be machined to a desired configuration along its length. In either situation, the ends of the hardened configuration are cut off as shown in FIG. 9. The machinability of the present electrode is substantially improved over the glassy carbon electrodes. Glassy carbon electrodes are extremely hard, and machining glassy carbon takes a relatively long time and usually causes substantial wear and damage to the machine tools. The present electrode can be machined quickly without damage to the machine tools because the bonding material is relatively soft compared to glassy carbon.

The end of the resulting electrode core which will become the electrode face 30 (FIG. 1) is polished. Either before or after polishing the electrode face end of the core, a jacket 28 of insulation is attached to the exterior of the core 26, as shown in FIG. 1. The jacket 28 of insulating material may simply be another layer of nonconductive resin material applied to the exterior of the hardened fiber and resin configuration. The metallic plate 34 (FIG. 2) is attached to the opposite end of the electrode by plating. The conductor 36 is attached to the metallic plate 34.

It is apparent that the foregoing steps of the presently preferred method for manufacturing the electrode are relatively simply and quickly accomplished, resulting in a low cost electrode 20.

Another embodiment 60 of the electrode of the present invention is illustrated in FIG. 10. The electrode 60 employs a central electrode conducting core 62 and a plurality of radially spaced concentric electrode conducting ring cores 64 and 66. Insulating material, preferably bonding material, is formed in concentric insulating rings 68, 70 and 72 intermediate the center conducting core 62 and ring conducting cores 64 and 66 and exterior of the outermost ring conducting core 66.

Fabrication of the electrode 60 proceeds by first forming the center conducting core 62 in the manner previously described. Thereafter, a concentric ring of insulating bonding material 68 is applied to the center core 62 and allowed to harden. Thereafter, another bundle of fibers is attached to the draw wire and the fibers are impregnated with resin bonding material. The fibers are generally distributed around the outer periphery of the electrode composite structure defined by portions 62 and 68. The fibers forming the first concentric ring 64 are thereafter drawn through a larger form to evenly distribute the fibers around the periphery of the insulating ring 68 and to generally align them in the concentric ring 64. Thereafter, the second insulating ring 70 is attached and allowed to harden. A similar procedure occurs with respect to the core ring 66 and the insulating ring 72 and is repeated until the desired number of ring electrodes have been formed on the electrode 60.

Of course, the center core electrode 62 and each of the ring electrodes 64 and 66 independently achieves the same desirable features as have been previously described in conjunction with the electrode 20. Separate electrical connections are made to each of the center core and the ring cores by plating conductors thereto in a manner similar to that described in conjunction with FIG. 2.

One example of a composite ring structure electrode similar to that shown at 60 is as follows. The center conducting core and the concentric conducting ring cores were formed of strands of Union Carbide "Thornel" 50 (PAN) carbon fiber grade WYR 15 1/0 material. Each strand consisted of six thousand fibers. The same type of resin bonding material was used in the electrical conducting cores as was used in forming the electrically insulating concentric rings. That resin was a Plasticrafts polyester impact resin. Initially, a center conductive core was formed using four strands of carbon fibers. The resulting diameter was 0.110 inches. A first insulating ring was next formed on the center conducting core. The resulting diameter of the composite structure at this point was 0.140 inches. A first conductive ring core was next added utilizing eight strands of carbon fibers. The resulting composite diameter was 0.196 inches. A second insulating ring was added and the resulting composite diameter was 0.227. A second conducting ring core was added utilizing sixteen strands of carbon fibers. The resulting diameter was 0.307 inches. Next, a third insulating ring was added and the resulting composite diameter was 0.350 inches. A third concentric ring was next added utilizing thirty-two strands of carbon fibers. The resulting diameter was 0.419 inches. Finally, a last insulating ring was attached and the final resulting composite diameter was 0.495 inches. After each step the resin was allowed to set before proceeding to the next step.

It is believed that the composite ring structure electrode, such as that shown in FIG. 10, will achieve improved performance with respect to the effects of diffusion. When the composite ring structure is rotated, the electroactive species in the solution quickly traverse each insulating ring and such diffusion helps recharge the boundary layer of electroactive species at the electrode faces of the conducting cores.

The excellent diffusion characteristics available from the present electrode and the ability to intercalate the carbon fibers with catalytic-type bonding materials makes the electrode of the present invention very useful in gas-liquid electrochemical reactions wherein the electroactive species is a gas.

Preferred embodiments of the present invention and their substantial improvements and advantages have been described with a degree of particularity. It should be understood, however, that the detailed description has been made by way of preferred example. Changes in details may be made without departing from the scope of the invention defined by the appended claims.

What is claimed is:

1. An electrode for electrochemical stripping analysis, comprising a core of a plurality of generally uniformly oriented and laterally spatially displaced electrically conductive fibers having a crystallographic structure of conducting planes of greatest electrical conductivity extending parallel to the longitudinal dimension of the fiber, an electrically insulating bonding material connected to and substantially completely filling the lateral spaces throughout the core between the laterally spatially displaced fibers and bonding the fibers into the core, an electrode face extending generally transversely with respect to and intersecting the ends of the fibers to maximumly expose the ends of the conducting planes for electron flow at the electrode face, and an electrical conductor directly electrically connected to each fiber at the other end of each fiber opposite of the electrode face, each fiber extending continuously between its ends at the electrode face and at the electrical conductor.

2. An electrode as defined in claim 1 further comprising an electrical insulating jacket surrounding the core at the electrode face and exposing substantially only the electrode face for stripping analysis.

3. An electrode as defined in claim 2 wherein the electrode face extends perpendicular to the fibers at the electrode face.

4. An electrode as defined in claim 3 wherein each fiber of the core is substantially the same length between its ends at the conductor and at the electrode face.

5. An electrode as defined in claim 1 further comprising a plurality of said cores, including a central core and at least one laterally displaced ring core surrounding the central core, and an insulation ring including electrically insulating bonding material connected intermediately of and completely filling the space between the central and ring cores at the electrode face.

6. An electrode as defined in claims 1 or 5 wherein said fiber is a carbon fiber.

7. An electrode as defined in claims 1 or 5 wherein said bonding material is one of an epoxy or polyester resin.

8. An electrode for electrochemical stripping analysis, and having an electrode face at which to perform the electrochemical reactions during the stripping analysis, comprising:

a plurality of uniformly oriented and laterally spatially displaced carbon fibers, each carbon fiber having paths of greatest electrical conductivity along its length defined by a crystallographic structure of each fiber having parallel conducting planes extending generally parallel to the longitudinal dimension of the fiber;

an electrical insulating resin material substantially completely surrounding each fiber and filling the lateral volume between the fibers and bonding the fibers permanently into a core;

a polished surface on the core intersecting substantially perpendicularly all of the fibers at ends thereof and substantially maximumly exposing the ends of the conducting planes of the fibers for electron flow at the polished surface, the polished surface defining the electrode face; and an electrical insulating jacket surrounding the core and confining electrochemical reactions substantially only to the electrode face; and electrical connection means for directly conducting current to the ends of all of the fibers which are opposite the ends of the electrode face, each fiber extending continuously between the electrical connection means and the electrode face.

9. An electrode as defined in claim 8 wherein the electrical connection means comprises a layer of electrically conducting material attached to each of the ends of the fibers of the opposite end of the core from the electrode face.

10. An electrode as defined in claims 8 or 9 further comprising a plurality of said cores including a generally cylindrical center core and at least one radially spaced and concentric ring core, and an insulating ring including an electrical insulating resin material ring connected intermediately of and completely filling the annular space between the central core and the ring core.

11. An electrode as defined in claims 1 or 8 wherein the fibers are generally parallelly oriented in the core.

12. An electrode as defined in claim 1 wherein each fiber of the core has substantially the same resistance between its ends at the conductor and at the electrode face.

* * * * *